(12) United States Patent
Kahn et al.

(10) Patent No.: US 7,045,639 B2
(45) Date of Patent: May 16, 2006

(54) METHOD FOR PURIFYING N-(2-HYDROXYETHYL)-2-PYRROLIDONE

(75) Inventors: Andrew P. Kahn, Eagleville, PA (US); Edward P. Carey, Atglen, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 15 days.

(21) Appl. No.: 10/941,134

(22) Filed: Sep. 15, 2004

(65) Prior Publication Data

US 2006/0058534 A1 Mar. 16, 2006

(51) Int. Cl.
*C07D 207/27* (2006.01)
(52) U.S. Cl. ................................... 548/551
(58) Field of Classification Search ......... 548/555, 548/551
See application file for complete search history.

(56) References Cited

U.S. PATENT DOCUMENTS

| | | | |
|---|---|---|---|
| 2,669,570 A | 2/1954 | Schnizer | 260/326.5 |
| 3,875,184 A | 4/1975 | Hort | 260/326.5 |
| 5,801,252 A | 9/1998 | Yano et al. | 548/554 |
| 2002/0139657 A1 | 10/2002 | Ugamura et al. | 203/81 |

FOREIGN PATENT DOCUMENTS

| GB | 1072429 | 6/1967 |
|---|---|---|
| GB | 1072429 C2 * | 6/1967 |

* cited by examiner

*Primary Examiner*—Joseph K. McKane
*Assistant Examiner*—Joseph R. Kosack
(74) *Attorney, Agent, or Firm*—Jonathan L. Schuchardt; John Calve

(57) ABSTRACT

A method for purifying N-(2-hydroxyethyl)-2-pyrrolidone (HEP) is disclosed. The method comprises crystallizing crude HEP to produce HEP crystals and a mother liquor, and separating the HEP crystals from the mother liquor. In one method of the invention, crystallization is induced by adding an HEP seed crystal to the crude HEP. In a preferred method, the crystallization is performed in the presence of 1–4 wt. % of added water. HEP can be successfully crystallized to a purity greater than 99.9%.

19 Claims, No Drawings

METHOD FOR PURIFYING N-(2-HYDROXYETHYL)-2-PYRROLIDONE

FIELD OF THE INVENTION

The invention relates to a method for purifying N-(2-hydroxyethyl)-2-pyrrolidone, an intermediate used in the manufacture of N-vinyl-2-pyrrolidone.

BACKGROUND OF THE INVENTION

The dehydration of N-(2-hydroxyethyl)-2-pyrrolidone (HEP) provides N-vinyl-2-pyrrolidone (NVP), a monomer used for making crosslinked or uncrosslinked polyvinylpyrrolidones, vinyl pyrrolidone-vinyl ester copolymers, and other valuable polymers. The polymers are used in beverage clarification, hair care, pharmaceutical tablet binding, and other industrial applications.

HEP is commercially available and is often made by reacting gamma-butyrolactone (GBL) with monoethanolamine (2-aminoethanol). It is normally purified by distillation (see U.S. Pat. No. 3,875,184 and U.S. Pat. Appl. Publ. 2002/0139657). The initial reaction product of GBL and 2-aminoethanol is N-(2-hydroxyethyl)-4-hydroxybutryamide, hereinafter "HEHBA," which undergoes an intramolecular dehydration reaction to give HEP. Because HEHBA is not easily separated from HEP by distillation, even a distilled HEP product will normally contain traces of HEHBA. The distilled HEP product also usually contains traces of 2-pyrollidone ("2-Py"), a hydrolysis by-product.

HEHBA, 2-Py, and other HEP impurities are preferably minimized because they will eventually contaminate the desired N-vinyl-2-pyrrolidone monomer. Particularly for pharmaceutical applications, it is crucial to have very pure N-vinyl-2-pyrrolidone. Thus, the industry would benefit from better ways to purify HEP.

HEP, a liquid at room temperature, has a nominal freezing point of 20° C. We found that HEP will crystallize upon prolonged standing, and its purity level can be raised simply by separating the resulting solids from any remaining mother liquor. This observation prompted us to devise conditions under which HEP can be effectively and efficiently purified by crystallization.

SUMMARY OF THE INVENTION

The invention is a method for purifying N-(2-hydroxyethyl)-2-pyrrolidone (HEP). The method comprises: (a) crystallizing crude HEP to produce HEP crystals and a mother liquor; and (b) separating the HEP crystals from the mother liquor. In one method of the invention, crystallization is induced by adding an HEP seed crystal to the crude HEP. In a preferred method, the crystallization is performed in the presence of 1–4 wt. % of added water. We surprisingly found that HEP can be successfully crystallized to a purity level in excess of 99.9%.

DETAILED DESCRIPTION OF THE INVENTION

N-(2-Hydroxyethyl)-2-pyrrolidone (HEP) is commercially available from BASF Corporation and International Specialty Products. It can also be made by well-known processes, particularly the reaction of gamma-butyrolactone and 2-aminoethanol (see, e.g., U.S. Pat. Nos. 2,669,570 and 5,801,252, the teachings of which are incorporated herein by reference). The source of the HEP is not critical. The method of the invention will benefit most commercial and non-commercial sources of HEP.

HEP is normally purified by distillation during its manufacture. The method of the invention can be used instead of distillation. More preferably, however, crystallization supplements distillation as a way to make pure HEP. Usually, a relatively simple distillation provides HEP that is pure enough to benefit from the crystallization method. As used herein, "crude HEP" refers to any HEP used as the starting material for a crystallization of the invention.

Crystallization is performed using well-known techniques and equipment. Usually, the crude HEP is chilled in a suitable vessel under conditions effective to promote HEP crystal growth. The crude HEP is preferably cooled to a temperature in the range of 0° C. to −20° C., more preferably in the range of −5° C. to −15° C., to promote crystallization. The crystals are then separated by any suitable means (e.g., filtration, decantation, centrifugation, or a combination of these methods) from the resulting mother liquor. After the crystals are separated from the mother liquor, the mother liquor can be further chilled to induce more crystal growth. The isolated crystals are conveniently recovered as a liquid by allowing them to warm to room temperature. Multiple crystallization steps can be used if desired to further enhance purity.

Crystallization is preferably induced by adding an HEP seed crystal to the crude HEP. A suitable seed "crystal" can be made simply by chilling commercial HEP until it freezes. As Examples 1–2 below show, crude HEP can be crystallized even at room temperature by adding a seed crystal and waiting for crystal growth to occur (typically 5–10 days).

Ideally, crystallization is performed quickly, i.e., within a few hours rather than a week or more. In one preferred method, the crystallization is performed in the presence of added water. The amount of added water is preferably 1 to 4 wt. % based on the amount of crude HEP. A more preferred range is from 2 to 3 wt. %. When water is added, it is preferred to chill the crude HEP to accelerate crystallization. Preferably, the mixture is chilled to less than −5° C., more preferably less than −10° C. HEP crystallizations in the presence of water can be further accelerated, if desired, by adding an HEP seed crystal to the mixture as described earlier.

We surprisingly found that adding an effective amount of water promotes a more porous crystal structure that allows the mother liquor to drain efficiently from the crystallized HEP and avoids entrapment of impurities in the crystals. As Examples 4–5 and Table 3 show, the purity level of even previously crystallized HEP can be further improved by recrystallizing it in the presence of added water.

We found that simply chilling HEP in the absence of water is generally ineffective for delivering a desired purity. As illustrated by Comparative Example 3, below, HEP usually supercools, then freezes quickly into a solid mass that contains occluded impurities. The solid mass melts rapidly upon warming to give impure HEP liquid and solids that still contain trapped impurities. In other words, the freeze/melt cycle does not significantly change the purity level of either phase, and no purification is achieved.

The method of the invention can provide highly pure HEP. Preferably, the HEP crystals have a purity greater than 99%, more preferably greater than 99.9%. As Example 5 demonstrates, a previously crystallized HEP sample of purity 99.85% could be upgraded to 99.95% purity using a single crystallization stage with the addition of 2 wt. % water. Interestingly, adding water into the crystallization method does not increase the amount of water present in the HEP crystals (see Table 3). The water level in the crystallized HEP stayed constant at 0.03 wt. %, even when 2 wt. % water was added for the crystallization.

Crystallization gives HEP with reduced levels of HEHBA, 2-Py, and other impurities that remain in HEP even after distillation. As noted earlier, HEP is an intermediate used in the manufacture of N-vinyl-2-pyrrolidone (NVP). Impurities in HEP will tend to survive the dehydration step and will carry over into the resulting NVP product. For many NVP polymer applications, particularly in the pharmaceutical industry, highly pure NVP is required. Starting with pure HEP makes it easier to manufacture highly pure NVP.

The following examples merely illustrate the invention. Those skilled in the art will recognize many variations that are within the spirit of the invention and scope of the claims.

EXAMPLE 1

Crystallization of Crude HEP at Room Temperature using an HEP Seed Crystal

A commercial sample of HEP is analyzed by gas chromatography (GC); results appear in Table 1. A seed crystal of HEP is added to induce crystallization. After standing for 10 days at room temperature, crystallization occurs. The mother liquor is decanted, and crystallized HEP is recovered. The results of analysis of both the mother liquor and the crystallized HEP are shown in Table 1. The results demonstrate that the purity level of HEP can be raised significantly by crystallization. In particular, the levels of 2-Py, HEHBA, water, and other impurities can be reduced. Interestingly, HEHBA was undetectable in this commercial HEP sample; detecting it becomes easier after the HEHBA is concentrated in the mother liquor.

TABLE 1

Results of GC Analysis of HEP Samples

| Wt. % of: | Commercial HEP | Crystallized HEP | Mother Liquor |
| --- | --- | --- | --- |
| HEP | 98.82 | 99.35 | 96.92 |
| 2-Py | 0.18 | 0.10 | 0.43 |
| HEHBA | 0 | 0 | 0.09 |
| other | 0.92 | 0.50 | 2.39 |
| water | 0.08 | 0.05 | 0.16 |

EXAMPLE 2

Crystallization of Crude HEP at Room Temperature using an HEP Seed Crystal

Example 1 is repeated with a different HEP sample, and the results are summarized in Table 2. The levels of 2-Py, HEHBA, water, and other impurities are substantially reduced.

TABLE 2

Results of GC Analysis of HEP Samples

| Wt. % of: | Commercial HEP | Crystallized HEP | Mother Liquor |
| --- | --- | --- | --- |
| HEP | 99.56 | 99.77 | 97.90 |
| 2-Py | 0.02 | 0 | 0.07 |
| HEHBA | 0 | 0 | 0.05 |
| other | 0.32 | 0.15 | 1.40 |
| water | 0.10 | 0.08 | 0.58 |

COMPARATIVE EXAMPLE 3

Attempted Crystallization of HEP at Reduced Temperature

A previously crystallized sample of HEP (purity level: 99.85%) is chilled over 2–3 hours. A steel rod is used to try to induce crystal formation. When the temperature reaches −6° C., the sample freezes to a solid mass. Upon warming, the mass melts rapidly to give HEP liquid and solids of substantially the same composition. No purification is achieved.

EXAMPLE 4

Crystallization of HEP at Reduced Temperature in the Presence of Added Water

Example 3 is repeated, except that water (1.0 wt. %) is added to the previously crystallized HEP prior to chilling it. The mixture is slowly cooled. HEP crystals form after about 2 h and at −11° C. Importantly, the mixture remains stirrable, and the crystals are isolated from the mother liquor. GC analysis is used to compare the purity of the crystallized HEP and mother liquor with that of the crude HEP (see Table 3). Adding water helps to avoid trapping of mother liquor in the HEP crystals, and the purity level of the already-pure HEP increases marginally to 99.88%.

EXAMPLE 5

Crystallization of HEP at Reduced Temperature in the Presence of Added Water

Example 4 is repeated, except that the amount of water added is 2.0 wt. %. HEP crystals form after about 5 h and at −11° C. The mixture is a readily stirrable slush, and the crystals are easy to isolate from the mother liquor. The resulting crystals are easy to handle because they do not melt rapidly after draining the mother liquor. GC analysis (Table 3) shows that the purity level of even a relatively pure sample of HEP can be raised significantly by crystallization in the presence of 2 wt. % added water. Interestingly, the water level in the crystallized HEP stays at 0.03 wt. %; it is unaffected by using 1 wt. % water in the crystallization or by increasing the amount of water to 2 wt. %.

TABLE 3

Results of GC Analysis of HEP Samples

| Wt. % of: | Starting HEP | Crystallized HEP from Ex. 4 | Crystallized HEP from Ex. 5 |
| --- | --- | --- | --- |
| HEP | 99.85 | 99.88 | 99.95 |
| 2-Py | 0 | 0 | 0 |
| HEHBA | 0 | 0 | 0 |
| other | 0.12 | 0.09 | 0.02 |
| water | 0.03 | 0.03 | 0.03 |

The preceding examples are meant only as illustrations. The following claims define the invention.

We claim:

1. A method which comprises: (a) crystallizing liquid, crude N-(2-hydroxyethyl)-2-pyrrolidone (HEP) by adding an HEP seed crystal to produce HEP crystals and a mother liquor; and (b) separating the HEP crystals from the mother liquor.

2. The method of claim 1 wherein the crystallization is performed at room temperature.

3. The method of claim 1 performed in the presence of 1 to 4 wt. % of water based on the amount of crude HEP.

4. The method of claim 3 performed in the presence of 2 to 3 wt. % of water based on the amount of crude HEP.

5. The method of claim 3 wherein the crude HEP/water mixture is chilled to less than −5° C. to induce crystallization.

6. The method of claim 5 wherein the crude HEP/water mixture is chilled to less than −10° C. to induce crystallization.

7. The method of claim 5 wherein the HEP crystals have a purity greater than 99%.

8. The method of claim 5 wherein the HEP crystals have a purity greater than 99.9%.

9. A method which comprises: (a) crystallizing liquid, crude N-(2-hydroxyethyl)-2-pyrrolidone (HEP) in the presence of 1 to 4 wt. % of water based on the amount of crude HEP at a temperature less than −5° C. to produce HEP crystals and a mother liquor; and (b) separating the HEP crystals from the mother liquor, wherein the HEP crystals have a purity greater than 99%.

10. The method of claim 9 wherein the crystallization is performed in the presence of 2 to 3 wt. % of water.

11. The method of claim 9 wherein the crystallization is performed at a temperature less than −10° C.

12. The method of claim 9 wherein the HEP crystals have a purity greater than 99.9%.

13. A method which comprises: (a) crystallizing liquid, crude N-(2-hydroxyethyl)-2-pyrrolidone (HEP) in the presence of 1 to 4 wt. % of water based on the amount of crude HEP to produce HEP crystals and a mother liquor; and (b) separating the HEP crystals from the mother liquor.

14. The method of claim 13 wherein the crude HEP is crystallized in the presence of 2 to 3 wt. % of water based on the amount of crude HEP.

15. The method of claim 13 wherein the crude HEP/water mixture is chilled to less than −5° C. to induce crystallization.

16. The method of claim 15 wherein the crude HEP/water mixture is chilled to less than −10° C. to induce crystallization.

17. The method of claim 13 wherein the HEP crystals have a purity greater than 99%.

18. The method of claim 13 wherein the HEP crystals have a purity greater than 99.9%.

19. The method of claim 13 wherein crystallization is repeated until HEP of a desired purity is obtained.

* * * * *